United States Patent
Sundstrom et al.

(10) Patent No.: US 11,311,850 B2
(45) Date of Patent: Apr. 26, 2022

(54) DIAMOND COMPOSITES BY LITHOGRAPHY-BASED MANUFACTURING

(71) Applicant: SANDVIK INTELLECTUAL PROPERTY AB, Sandviken (SE)

(72) Inventors: Johan Sundstrom, Stockholm (SE); Malin Martensson, Nacka (SE)

(73) Assignee: Sandvik Intellectual Property AB, Sandviken (SE)

( * ) Notice: Subject to any disclaimer, the term of this patent is extended or adjusted under 35 U.S.C. 154(b) by 1078 days.

(21) Appl. No.: 15/754,316

(22) PCT Filed: Aug. 25, 2016

(86) PCT No.: PCT/EP2016/070099
§ 371 (c)(1),
(2) Date: Feb. 22, 2018

(87) PCT Pub. No.: WO2017/032842
PCT Pub. Date: Mar. 2, 2017

(65) Prior Publication Data
US 2018/0250647 A1    Sep. 6, 2018

(30) Foreign Application Priority Data
Aug. 26, 2015  (EP) .................... 15182540

(51) Int. Cl.
*B33Y 10/00*  (2015.01)
*B29C 64/129*  (2017.01)
(Continued)

(52) U.S. Cl.
CPC ............... *B01J 3/062* (2013.01); *A61L 27/08* (2013.01); *B22F 10/10* (2021.01); *B29C 64/129* (2017.08); *B32B 18/00* (2013.01); *B33Y 10/00* (2014.12); *B33Y 80/00* (2014.12); *C04B 35/117* (2013.01); *C04B 35/52* (2013.01); *C04B 35/573* (2013.01); *C04B 35/58071* (2013.01); *C04B 35/6269* (2013.01); *C04B 35/634* (2013.01);
(Continued)

(58) Field of Classification Search
CPC ....... B33Y 10/00; B29C 64/00; B29C 64/124; B29D 64/129
See application file for complete search history.

(56) References Cited

U.S. PATENT DOCUMENTS

| | | | |
|---|---|---|---|
| 7,927,538 B2 | 4/2011 | Mozner et al. | |
| 2006/0191723 A1 | 8/2006 | Keshavan | |

(Continued)

FOREIGN PATENT DOCUMENTS

| | | |
|---|---|---|
| EP | 0196777 A1 | 10/1986 |
| EP | 2915663 A2 | 9/2015 |
| WO | 2014161816 A2 | 10/2014 |

OTHER PUBLICATIONS

"PIM parts and Ceramics debinding processs & Supercritical CO2 equipment", Aug. 30, 2011, URL: http://www.separex.fr/download/category/8-applications.html?download=2:ceramics-debinding-applications. [retrieved on Feb. 2, 2016] paragraph [0001].

*Primary Examiner* — Pegah Parvini
(74) *Attorney, Agent, or Firm* — Corinne R. Gorski (57) ABSTRACT

A lithography based method for the manufacture of diamond composite materials in which green bodies are prepared by a layer-by-layer construction with resulting green bodies de-bound and sintered to achieve a dense high hardness material.

9 Claims, 8 Drawing Sheets

(51) Int. Cl.

| | |
|---|---|
| *B01J 3/06* | (2006.01) |
| *C04B 35/52* | (2006.01) |
| *C04B 35/573* | (2006.01) |
| *C04B 35/638* | (2006.01) |
| *C04B 35/645* | (2006.01) |
| *A61L 27/08* | (2006.01) |
| *C04B 35/626* | (2006.01) |
| *B32B 18/00* | (2006.01) |
| *B33Y 80/00* | (2015.01) |
| *C04B 35/63* | (2006.01) |
| *E21B 10/46* | (2006.01) |
| *E21B 10/55* | (2006.01) |
| *B22F 10/10* | (2021.01) |
| *C04B 35/117* | (2006.01) |
| *C04B 35/58* | (2006.01) |
| *C04B 35/634* | (2006.01) |

(52) U.S. Cl.
CPC ........ *C04B 35/638* (2013.01); *C04B 35/6316* (2013.01); *C04B 35/645* (2013.01); *C04B 35/6455* (2013.01); *E21B 10/46* (2013.01); *E21B 10/55* (2013.01); *C04B 2235/3826* (2013.01); *C04B 2235/427* (2013.01); *C04B 2235/428* (2013.01); *C04B 2235/48* (2013.01); *C04B 2235/5436* (2013.01); *C04B 2235/5472* (2013.01); *C04B 2235/608* (2013.01); *C04B 2235/6026* (2013.01); *C04B 2235/616* (2013.01); *C04B 2235/6562* (2013.01); *C04B 2235/6567* (2013.01); *C04B 2235/661* (2013.01); *C04B 2235/725* (2013.01); *C04B 2235/77* (2013.01); *C04B 2235/80* (2013.01); *C04B 2235/85* (2013.01); *C04B 2235/963* (2013.01); *C04B 2235/9638* (2013.01); *C04B 2237/363* (2013.01); *C04B 2237/365* (2013.01); *C04B 2237/582* (2013.01); *C04B 2237/704* (2013.01)

(56) References Cited

U.S. PATENT DOCUMENTS

| | | | |
|---|---|---|---|
| 2007/0269604 A1* | 11/2007 | Francis | H01L 21/4871 427/331 |
| 2008/0316595 A1* | 12/2008 | Van Herpen | G02B 5/0891 359/359 |
| 2010/0029801 A1* | 2/2010 | Moszner | G03F 7/0037 522/167 |
| 2010/0279007 A1 | 11/2010 | Briselden et al. | |
| 2011/0256371 A1* | 10/2011 | Layyous | C23C 28/341 428/216 |
| 2012/0010066 A1 | 1/2012 | Fischer et al. | |
| 2013/0167447 A1* | 7/2013 | Webb | C04B 35/52 51/298 |
| 2016/0015483 A1* | 1/2016 | Kumar | A61C 8/0075 606/301 |

\* cited by examiner

DIAMOND COMPOSITES BY LITHOGRAPHY-BASED MANUFACTURING

RELATED APPLICATION DATA

This application is a § 371 National Stage Application of PCT International Application No. PCT/EP2016/070099 filed Aug. 25, 2016 claiming priority to EP Application No. 15182540.3 filed Aug. 26, 2015.

FIELD OF DISCLOSURE

The present disclosure relates to diamond composites manufactured from a layerwise based building method and to aspects associated with such a method.

BACKGROUND ART

A variety of different diamond materials have been developed for use in applications such as wear parts or for objects in cutting, turning, drilling and the processing of hard materials including rock and in particular metal alloys such as steel. The diamond density as well as the properties of the surrounding matrix are important characteristics for their suitability for wear resistant tools. The most common diamond material used in cutting tools is PCD (polycrystalline diamond bodies) which exhibit substantial abrasion resistance and hardness but contain catalytic metals such as cobalt, iron and/or nickel. Accordingly, such materials exhibit low thermal stability. Due to manufacturing processes operating at extremely high pressures (above 5500 MPa) it is only possible to near net produce PCDs with simple geometries. Accordingly, further types of diamond material that are of increasing interest include silicon cemented diamond and silicon carbide diamond composites which, whilst having a lower diamond content relative to PCDs, are cobalt, nickel and iron free in addition to being thermally stable even at temperatures well above 1000° C. There exists a variety of different methods of manufacturing such materials using a silicon carbide matrix. Examples include hot isostatic pressure processing (HIP) in which a powdered batch of starting materials are subject to heat and pressure cycles as disclosed in WO 2014/161816.

More recently, the technique of rapid prototyping has been used in the preparation of high-strength ceramics, which produces a three-dimensional article in layers from a liquid slurry containing a curable monomer resin based on computer aided design data. US 2012/0010066 and U.S. Pat. No. 7,927,538 describe a stereolithographic preparation of ceramic shaped parts. Initially, a ceramic precursor compact (alternatively termed a green body) is prepared by light radiation curing a free-flowing ceramic slurry via a layer-by-layer stepwise build process. The resulting green body is then subjected to de-binding to remove the initial green body binder typically involving heating to temperatures in the region of 90° C. to 600° C. The resulting white (alternatively termed brown) body is then sintered at high firing temperatures to compact and solidify during a significant volume decrease whereby the densified ceramic exhibiting low porosity and high strength is provided.

However, conventional compaction manufacturing methods for use in generating high hardness composite bodies have problems as it is difficult to achieve surfaces and edged which are homogeneous and also as it is difficult to obtain defect free surfaces.

Furthermore, in conventional compaction techniques, especially in combination with granulated powders, the compaction of the edges are usually poorer resulting in more defects resulting in a lower sintered diamond density in these areas. Yet another problem with conventional compaction techniques is the wear of the press tools, which apart from the cost, also introduce impurities on the green bodies, which will maintain in the final product. The amount of impurities is critical in e.g. medical or food industry and uses.

SUMMARY OF THE DISCLOSURE

The aim of the present disclosure is to solve or at least reduce the above-mentioned problems. Thus, it is therefore an objective of the present disclosure to provide a superhard component such as tool or tool insert for possible use as a wear part or cutting element that is resistant to fracture, spalling, chipping and general wear during the working life of the component. In particular, it is a specific objective to provide a diamond composite work tool such as a cutting element or a wear part or a tool insert exhibiting an optimised/maximised average working lifetime. It is a further objective to provide a wear resistant tool component that exhibits even wear behaviour in three dimensions. It is a yet further objective to provide a method of manufacturing a superhard wear resistant composite body via an efficient use of materials that minimises or eliminates degradation or wear of tooling used in the manufacture process.

The objectives are achieved by forming superhard materials, i.e. a diamond composite, from diamond particles via an initial lithographic layer-by-layer construction of a body from a free-flowing slurry comprising diamond particles followed by debinding, infiltration and sintering processes.

The term 'lithographic based manufacturing' encompasses stereolithography, 3-D building, additive manufacturing (AM) or 3-D 'printing' in which solid or semi-solid layers are constructed from a liquid slurry containing a curable monomer or polymer resin, i.e. a polymerisable binder, on the basis of computer aided design (CAD) data. The term 'diamond composite' (also known as cemented diamonds) used herein encompasses superhard materials incorporating diamond particles within a matrix or binder phase, the diamond content may be in the range of from 30 to 85 vol %. The term encompasses materials formed as a mass of diamond grains (also called diamond particles) inter-bonded via a binder, such as silicon carbide, or with the diamond grains embedded in a metal matrix or in a mixture of a metallic and a carbide binder phase. Thus, the diamond particles are bonded to the matrix by sintering. The term 'layered structure' used herein refers to the profile of the body and post sintered article in a plane extending through the body perpendicular to the plane within which the slurry is irradiated during the stepwise layered lithographic building. It is to be understood that the layered structure comprises more than one layer of diamond particles and binder.

Lithographic manufacturing according to the subject disclosure is advantageous over conventional compaction techniques typically employed for diamond composite materials. In particular, the lithographic method may be undertaken conveniently with low amounts of impurities (<2 wt %) otherwise introduced by the abrasion of the diamond particles to die walls, moulding tools, blending and granulation equipment and without the need for a die that is used in conventional pressing processes and is subject to accelerated wear and requires regular replacement with high costs. The present layer-wise construction via a polymerisable binder enables the creation of green bodies (greens) and pre-sintered, de-bound bodies (termed white or brown bodies)

having complex 3D geometries including in particular complex internal and external shape profiles. The present methodology is also advantageous to provide uniform density green bodies and resulting sintered diamond composite bodies. This is to be contrasted with conventional pressing techniques using granulated powder where it is common for the green bodies to contain uncrushed granules that are then filled with infiltrant (typically silicon) resulting in undesirable infiltrant (Si—) lakes and accordingly discontinuities in the surface regions and in particular cutting edges that leads to premature component wear via chipping, splitting or fracture.

The resulting sintered structures according to the subject disclosure comprise readily identifiable layers in which each layer comprises a uniform thickness or at least a predetermined thickness according to the operating conditions of the lithographic apparatus and method. The identifiable layers contain diamond particles and binder matrix. The layered structure consist of layers rich in diamond particles which have a thickness range of 25-200 microns, such as 25-50 micron or such as 50-100 microns which have binder-matrix rich layers in between. The binder matrix rich layers have the thickness in range of 1-15 microns such as 1-4 microns or 2-8 microns or 5-10 or 6-15 microns. By altering the thickness and the concentration of the diamond and binder matrix rich layers, the wear, crack propagation and heat conductivity properties can be tailored more easily. By a diamond particle rich layer is meant that the layer contains more than 30 vol % diamond particles and by binder-matrix rich layer is meant that the layer contains less than 30 vol % diamond particles. The uniform distribution of the diamond particles within the sintered bodies provides a work element (such as wear part or cutting tool or cutting tool insert) that exhibits even wear behaviour in use. This uniform distribution within the sintered diamond composite body is confirmed by SEM imaging as described herein.

Additionally, the present sintered bodies may be considered to comprise an optimised surface roughness, with roughness being determined, in part, by the particle size distribution of the diamond particles in the free-flowing slurry batch, and in the green and white bodies. The surface area roughness (Sa) of the obtained sintered white bodies may be <4 microns, such as <3 microns, the surface roughness can be measured by using conventional surface measuring instruments The uniform distribution of the diamond particles within the resulting composites is due, in part, to the manufacture of green bodies via the layered lithographic construction followed by the de-binding of the polymerised binder. It has been observed that the de-bound brown bodies are optimised for the infiltration by the infiltrant binder (for example silicon) due to the internal network of open pore channels resultant from the loss/de-binding of the polymer. A further particular advantage of the present method is the configuration to selectively adjust the magnitude, density and layout of the infiltration channels within the brown body by selectively adjusting the particle size distribution and in particular by blending particles of different average size during the creation of the homogenous free-flowing slurry. Incorporating particles of different size distributions is also advantageous to optimise packing of the green and white bodies to achieve a uniform particle distribution within the final sintered article. The white bodies resultant from the de-binding step exhibit no cracks as can be seen from CT analysis as described herein. This initial processing flexibility together with possible tailoring of the infiltration/sintering stages provides a process that is optimised to achieve a desired density of the final composite body with regard to the distribution of the superhard diamond particles within the binder matrix.

According to a first aspect of the present disclosure, there is provided a method of preparing a diamond composite comprising:
 preparing a slurry containing a polymerisable binder, an initiator and diamond particles;
 forming a layered structure green body by stepwise irradiation curing of the slurry containing diamond particles and a temporary binder and an initiator;
 forming a white body comprising at least 30 vol % diamond particles by de-binding the layered structure green body;
 introducing an infiltrant to the white body and
 sintering the white body by heating the white body as an initial stage up to a maximum sintering temperature by incremental temperature increase at a rate of 10 to 60° C./min at a first pressure.

The present method will provide for that during the introduction of an infiltrant and sintering process, the size and shape of the de-bound green body is maintained and the dimensions of the final obtained diamond composite have changed with less than 1.5% when comparing with the dimensions, such as height, length and/or diameter of the green body. Furthermore, the diamond particle size is maintained or decreased, thus the present disclosure does not have any grain growth of the diamond particles.

The de-binding step may be performed in a nitrogen, a hydrogen, an argon or a mixture thereof atmosphere or in air by slowly, typically between 0.1-2° C./min, by heating the green body to temperatures between 200-600° C., depending on the atmosphere and the polymerisable binders present.

According to the present method, the maximum sintering temperature is above the melting temperature of the infiltrant in order for the infiltrant to be in a melted stage.

The present method may comprise a pre-sintering step which may be performed by heating the white body obtained after the de-binding step in an inert atmosphere or in vacuum up to temperatures between 600° C. to 1500° C. with holding times at maximum temperature of between a few minutes to an hour.

Optionally, the diamond particles may comprise a particle size of less than 200 µm, 150 µm, 100 µm and/or 80 µm. Optionally, the diamond particles may comprise a particle size in the range 0.5 µm to 100 µm; 1 µm to 100 µm and/or 2 µm to 80 µm. In particular, the diamond particles may comprise a bi-modular or multi-modular particle size distribution. Optionally, at least one fraction of diamond particles comprising a particle size of less than 30, 20 or 10 µm and at least one fraction of diamond particles comprising a particle size of less than 100, 80, 70, 60 or 50 µm. Such an arrangement is advantage to optimise the packing of the diamond within the resulting green and white bodies and the final sintered articles.

The thickness of the diamond particles rich layers and the binder-matrix rich layers is determined by the building process, i.e. they depend on the apparatus and the illumination technique used and also on the maximum particle size in the slurry e.g. the maximum diamond particle size in the slurry must not exceed the thickness of the building layers. The thickness of the different layers may be varied during the layered building process thus allowing for a faster building in areas not so critical and a slower building in critical areas such as edges. According to one embodiment, the particle size and distribution may also be changed during the building of the layered structure by changing or mixing slurries having different diamond particle size distribution, thus yielding a continuous particle size gradient in building direction.

Optionally, the diamond particles comprises at least one fraction having a particle size of less than 10 μm and at least one fraction having a particle size of less than 50 μm. Optionally, the diamond particles comprise 10 to 30 wt % of the first fraction and 70 to 90 wt % of the second fraction. Optionally, the diamond particles comprises 20 wt % of diamond particles having an average particle size of 4 to 8 μm and 80 wt % of diamond particles having an average particle size of 20 to 30 μm. Optionally, the diamond may comprise a third fraction of diamond particles comprising an average particle size of 4 to 90 μm or 6 to 80 μm. Optionally, the diamond particle content comprises particles having an average particle size in the range 2 to 200 μm, such as 2 to 100 μm.

According to one embodiment, the diamond particles comprise a bi-modular or multi-modular size distribution to achieve a high density, wherein the weight fraction of the largest diamonds (LD)/sum of the weight fraction of the smaller diamonds (ΣSD) in the feed is typically ranging from 1.2 to 19. According to one embodiment of the present disclosure, the diamond particles comprise a low impurity (<5000 ppm) of catalytic metals including in particular Ni, Fe and Co. Optionally, the diamond particle content in the de-bound white body (alternatively brown body) is at least 30 vol %, such as at least 40 vol % and such as at least 50 vol % based on the total volume of material of the body.

Hence, the present method may also be said to be a lithographic based method wherein a diamond composite is prepared comprising the steps of: preparing a slurry including a polymerisable binder, a polymerisation initiator and diamond particles; forming a green body having a layered structure by stepwise irradiation curing the slurry; de-binding the green body to at least partially remove the binder from the diamond particles to form a white body; and sintering the white body to form the diamond composite having a layered structure.

The slurry exhibits low polymerisation shrinkage and accordingly enables the preparation of dimensionally stable and flexible green bodies exhibiting low deformation stress. The green bodies obtained via the lithographic layered construction are defect free, i.e. the green bodies contain low level of cracks and other defects and may even have no defects, with excellent adhesion achieved between the individual lithographically produced layers.

According to the method as defined hereinabove or hereinafter, the de-binding step may comprise: heating the green body up to a first maximum temperature by incremental temperature increase. Optionally, the de-binding is performed in an environment selected from nitrogen, argon, hydrogen and mixtures thereof. Air may also be used as an environment. Optionally, the maximum de-binding temperature is in a range 200° C. to 600° C., the de-binding temperature will depend on the environment in which the de-binding step is performed (gas used). Optionally, the incremental temperature increase comprises increments of 0.1 to 2° C./min.

According to one embodiment, the maximum de-binding temperature is in a range 200° C. 15 to 340° C. in air and the incremental temperature increase comprise increments of 0.1 to 2° C./min. According to one embodiment of the present method as defined hereinabove or hereinafter, the de-binding comprises one, two or three cycles of heating in which the temperature is increased by increments separated by one or a plurality of holding times at which the temperature is maintained as an intermediate stage followed by continued increase in the temperature via the incremental change. Optionally, the maximum de-binding temperature may be 220° C. and/or 320° C. Optionally, an initial stage de-binding comprises heating up to a maximum heating temperature of 220° C. at 0.3° C./minute increments. Optionally, the de-binding comprises a second de-binding stage comprising heating the bodies up to a maximum temperature of 300 to 600° C. with temperature increments of 0.5 to 2° C./minutes.

According to the method as defined hereinabove or hereinafter, the step of de-binding may, instead of thermal treatment, comprise exposing the green body to a supercritical fluid. Optionally, the supercritical fluid is carbon dioxide having a critical temperature of 31° C. and a critical pressure of 7.38 MPa. Alternatively, other supercritical fluids may be single component fluids, binary or tertiary systems, each based on alkanes, alkenes, fluorinated and/or hydrofluorinated alkanes. Optionally, the de-binding step may also comprise heating in combination with supercritical solvent extraction.

According to the method as defined hereinabove or hereinafter, the binder is removed during the de-binding step. The removal of the binder may be partial and the degree of de-binding of the polymerisable binders in the green body during the first step may be in the range of range 35 to 75% by weight or 40 to 80% by weight. The remainder of the binder may act as a 'carbon source', i.e. the carbon of the binder will be used instead of the diamond particles during the infiltration step when a carbide former is used as an infiltrant, which provides that less diamond particles are used.

According to one embodiment of the method as defined hereinabove or hereinafter, the step of sintering comprises: introducing an infiltrant to the white body; heating this body as an initial stage up to a maximum sintering temperature, which temperature is above the melting point of the infiltrant, via incremental temperature increase at a first pressure. As an optional step, the body may then be heated continuously in a further stage at a second pressure being greater than the first pressure. The sintering stage may comprise exposing the de-bound white body to an infiltrant such as silicon. The white/brown body may be coated or brought into contact with the infiltrant. The infiltrant may comprise silicon having a purity greater than 99% and may be present in large excess (greater than 200 wt % excess). The infiltrant may comprise Si as the main constituent. According to one embodiment of the method as defined hereinabove or hereinafter, the Si-infiltration stage comprises heating the white/brown body to a temperature above 1500° C., 1600° C., 1650° C. or 1700° C. Optionally, the white/green body may be immersed in an argon environment at a pressure greater than 5, 7 or 9 MPa optionally for a period of 5, 10, 15 or 20 minutes to assist densification and reduce porosity in the final post-sintered composite article. Optionally, the maximum sintering temperature during the initial state is in the range 1500 to 1750° C. and the incremental temperature increase comprises increasing the temperature at a rate of 10 to 60° C./min, 10 to 40° C./min, 10 to 30° C./min or 10 to 20° C./min. According to one embodiment of the method as defined hereinabove or hereinafter, the initial de-binding stage is performed in air or flowing hydrogen at atmospheric pressure. Optionally, the second pressure at the second stage of the sintering/Si-infiltration densification step is at least 50% or 80% greater than the first pressure. Optionally, the infiltrant may be selected from silicon, silicon compositions, copper, copper alloys, aluminium and aluminium alloys.

Optionally, the maximum sintering temperature during the initial state will in the range of from 850 to 1750° C., i.e. above the melting temperature of the infiltrant.

According to a further aspect of the present disclosure there is provided a slurry for lithographic based manufacturing of a diamond composite comprising: a polymerisable binder; an initiator; and diamond particles. The binder is a polymerisable binder and may comprise at least one acidic monomer. Optionally, the binder may include monofunctional monomers or monofunctional polymers having at least one radially polymerisable group. Such monomers may comprise a —COOH, a —O—PO(OH)$_2$ or a —SO$_3$H group.

Optionally, the slurry comprises 70 to 90 wt % of diamond particles which corresponds to about 40 to 70 vol % relative the total volume of the slurry. Optionally, the slurry comprises a polymerisable binder content of 10 to 30 wt % which corresponds to about 30 to 60 vol % relative to a total volume of the slurry. Additionally, the diamond particle content within the resulting sintered composite may be in the range 20 to 60 vol %.

According to a further aspect of the present disclosure there is provided a diamond composite article formed from a lithographic based manufacturing method comprising: a layered structure resultant from a stepwise irradiation curing of a slurry containing diamond particles followed by de-binding and sintering.

According to a further aspect of the present disclosure there is provided use of diamond particles within a lithographic based manufacturing method to form a diamond composite article comprising: a layered structure resultant from i) a stepwise irradiation curing of a slurry containing the diamond particles followed by ii) de-binding and iii) sintering.

According to a further aspect of the present disclosure, there is provided a diamond composite article formed from a lithographic based manufacturing method comprising: a layered microstructure resultant from i) a stepwise irradiation curing of a slurry containing diamond particles followed by ii) de-binding and iii) Si-infiltration at vacuum and sintering at <150 bar.

According to yet another aspect of the present disclosure there is provided a diamond composite article having a diamond particle content between 30 and 65 vol % comprising: a layered microstructure having diamond rich layers with binder matrix rich layers in between wherein the diamond rich layers are in the range of 25 to 200 microns, such as 25 to 100 microns, and the binder matrix rich layers are in the range of 1 to 15 microns. According to one embodiment, the binder is SiC. According to yet another embodiment, the uniform surface area roughness <4 microns, such as <3 microns. Additionally, due to the method used, the deviation of the external features compared with the CAD-drawing is <1.5, such as <1%.

According to the present disclosure, there is also disclosed a diamond silicon carbide composite with a diamond content between 30 and 55 vol % having a layered microstructure consisting of diamond-SiC layers in the range of 25 to 100 microns with SiC enriched-layers of the range 1 to 15 microns in-between having a uniform surface area roughness <4 microns, such <3 microns.

Composite articles prepared according to the subject disclosure are particularly suitable as wear parts especially in corrosive and hot environments and also where a particular application demands low or very low impurity content. The present diamond composite, such as the diamond particle and silicon carbide composite, bodies exhibit optimised thermal stability, resistance to abrasive degradation and liquid corrosion such as exposure to acids and alkalis and extremely good heat conductivity. The wear parts may find particular application for metal and rock cutting. The present composites may also be suitable for medical implants and for cobalt free applications within the food industry. Additionally, the present sintered bodies having an optimised uniform distribution of composite components which may be desirable for application as jewelry.

Three-dimensional elements of the subject disclosure that comprise diamond particles bonded within a carbide matrix also exhibit good thermal conductivity. It is noted that polycrystalline diamonds (PCDs) that contain catalytic metals such as Co, Fe and Ni are not thermally stable. Additionally such materials according to conventional processing cannot be shaped conveniently and effectively which limits the three-dimensional geometry of resulting components. The surface roughness of the present components is also optimised in comparison to existing conventional manufacturing methods which is particularly important for diamond composites where grinding/milling is time consuming and inefficient.

The present layer-wise constructions are advantageous to create crack free green bodies that do not shrink appreciably during infiltration. The present method therefore provides optimised dimension control via the processing parameters and the selection of starting materials with regard to particle size distribution, concentrations, de-binding and sintering stages.

BRIEF DESCRIPTION OF DRAWINGS

A specific implementation of the present disclosure will now be described, by way of example only, and with reference to the accompanying drawings in which.

DETAILED DESCRIPTION OF DIFFERENT EMBODIMENTS OF THE DISCLOSURE

A diamond composite is manufactured using lithography and in particular stereolithography. The process comprises generally, in a first stage, irradiation, such as LED-radiation curing of a free-flowing slurry to create a geometric three-dimensional article in the form of a compact, alternatively termed a green body. In a second stage, the green body is subjected to a de-binding process to remove the binder to obtain a white (or brown) body. As a final stage, the white body is infiltrated and sintered to create the dense diamond composite. The sintered body may then be finished by grit blasting and/or acid etching to yield a final superhard diamond composite suitable for a variety of applications such as use as a high abrasion resistant body for processing hard materials such as alloys and rock.

With the aim of achieving a superhard diamond composite with low porosity, high density and a uniform distribution of the diamond grains within the sintered composite, bi-modular and multi-modular diamond feeds were prepared. Utilising a lithographic, and in particular a stereolithographic, process require dark raw materials such as silicon and/or dark carbides to be minimised within or excluded from the initial slurry. In particular, the slurry needs to be transparent or semi-transparent to allow transmission of the light radiation during the layer-by-layer stepwise building.

The present disclosure is illustrated by reference to the non-limiting examples 1 to 5 that include selectively the following preparation stages.

Diamond Powder Preparation

Diamond powders were dry blended together to form a uniform mixture. The final diamond mixture was a mixture of 80 wt % 20 to 30 μm and 20 wt % 4 to 8 μm diamonds of grade MBM-ULC and MBM-LC obtained from Diamond Innovations Inc., thus having a weight fraction LD/ESD of 4. This diamond mixture is referred to herein as a PSD1 feed. In addition, a PSD2 feed was prepared as described above using MBM-ULC and MBM-LC grades from Diamond Innovations Inc., but having a multi-modular diamond particle size distribution ranging from 2-80 μm with a weight fraction of LD/ESD of 1.6.

Slurry Preparation

Polycrystalline diamond slurries was prepared by mixing i) PS-m-FlEA (a reaction product of 1 mol phthalic acid anhydride with 1 mol 2-hydroxyethyl acrylate); NK-ester CBX-1N (pentaerythritol triacrylate monophthalate) at 70%, ii) solvents PEG-400 and PPG-400 respectively. A dispersant was introduced and the obtained composition was mixed homogeneously. A photo initiator K-69 (bis(4-methoxybenzoyl)diethylgermanium, Ivoclar Vivadent AG) or Irgacure 819 (bis(2,4,6-trimethylbenzoyl)phenylphosphine oxide, Ciba SC) was then added and dissolved by simple stirring. As a final stage, the diamond feed PSD1 was added and dispersed to create free-flowing homogeneous slurries. Diamond loading of the PSD1 feed was 80 wt % which corresponds to about 54 vol % and the binder content was approximately 20 wt % which corresponds to 46 vol %.

Lithographic Process and Apparatus—Green Building

Figure 1:
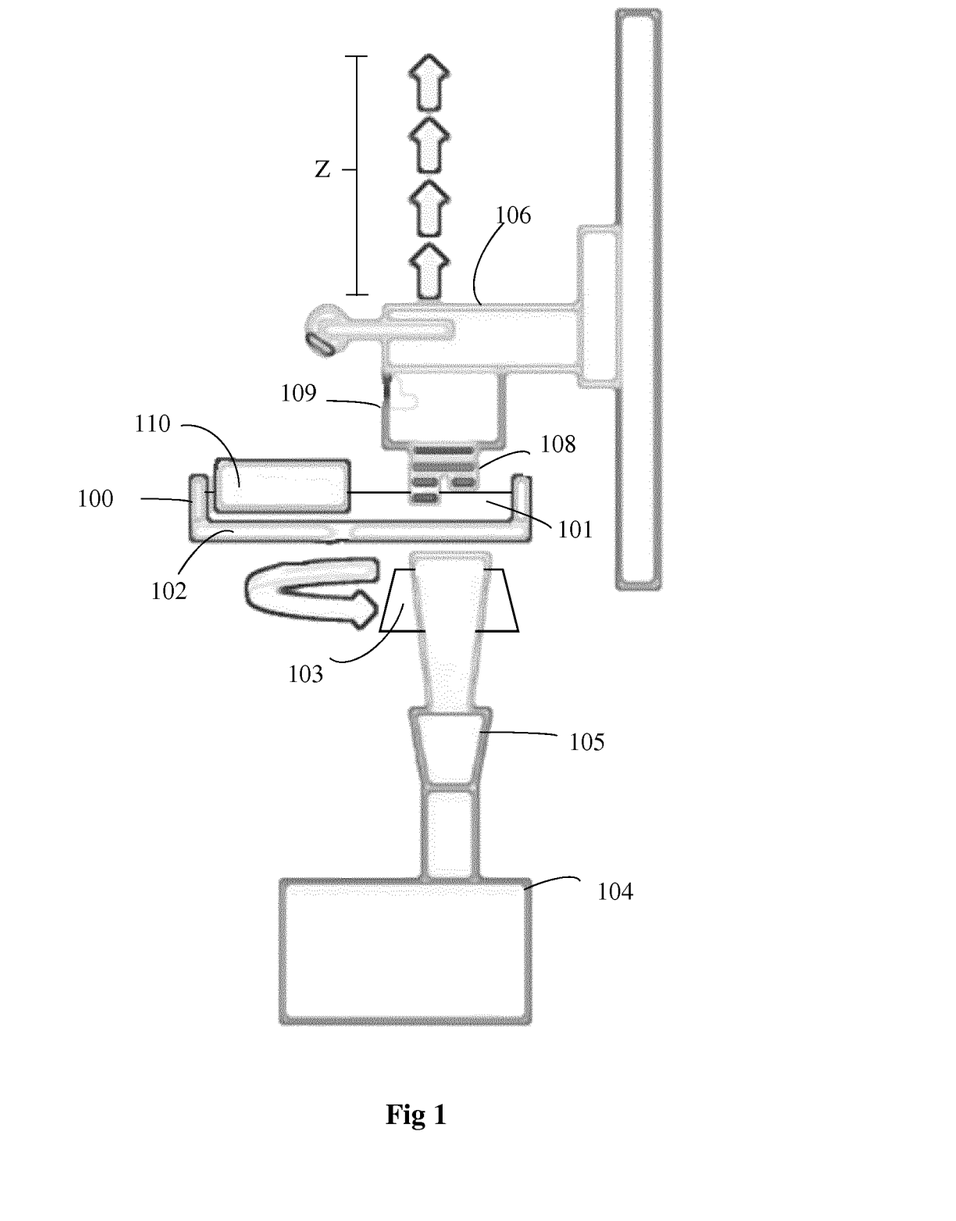
FIG. 1 is a schematic illustration of the lithography processing apparatus to create green bodies according to one aspect of the present disclosure.

The lithographic process and apparatus is described generally with reference to FIG. 1 and comprises a container 100 (or polymerization tank) for the slurry 101. Container 100 has a transparent window 102 through which slurry 101 is selectively irradiated and cured from below. A micromirror array 103 is moveably positioned underneath container 100 and is a computer controlled. A radiation source 104 directs irradiating energy (in the form of LED generated light) onto mirror 103. Accordingly an image of the mirror 103 is projected onto the slurry 101 via window 102 using an optical device (not shown). Arranged above container 100 is a substrate carrier 106 having a carrier plate 109 movable in a Z-direction which carries a building platform 109 on which the green body 108 is constructed layer-by-layer. The carrier plate 109 is immersed in slurry 101 until a distance between carrier plate 109 and an inner surface of the container 100 corresponds to the desired layer thickness to be produced. The slurry layer, between carrier plate 109 and the inner surface of container 100, is then selectively irradiated and cured through the transparent window 102 via mirror 103. Cured regions of the slurry 101 adhere to carrier plate 109 and are then raised from the container 100 in the Z-direction. More slurry is then spread across window 102 using a wiper blade 110 and the selective irradiation curing process is repeated to construct the desired three-dimensional article.

Greens were built according to the following stereolithographic parameters settings: lateral resolution 40 μm (635 dpi); number of pixel (X,Y) 1920×1080; building envelope (X,Y,Z) 76 mm×43 mm×150 mm; data format .stl (binary); slice thickness 25-100 μm; building velocity up to 100 slices per hour, 2.5-10 mm per hour; light source LED. After the building process, the greens are washed with organic solutions (washing agents) to remove excess slurry and create a fine surface finish.

De-Binding (Heat Treatment)

The de-binding was performed in air and involved slow temperature ramping at 0.3° C./minute intervals up to 220° C. and/or 320° C. The modest temperature increments were advantageous to avoid cracking of the greens during de-binding particularly as the washing agents tended to cause cracking during de-binding. The mass loss during de-binding differed depending on if the green had been cleaned or not after building and was between 8-11 wt %. Mass loss in wt % was calculated as ((m(built)−m(de-bound))/m(built))*100.

De-Binding (Supercritical Solvent)

De-binding trials using oscillating supercritical $CO_2$ with pressures of 30 MPa (300) bars and temperatures between 55-65° C. for 4.5 h up to 28.5 h were also undertaken. The resulting greens were crack free. Additionally, the resulting sintered composites exhibited no external cracks with no major defects detected. The supercritical solvent processing was undertaken in accordance with the parameter configuration as detailed in table 1.

TABLE 1

| | | | | | A22 | | | M220 | M220 | |
| | Process Step | Duration (min) | P200 $CO_2$ (Kg/h) | | Pressure (MPa) | H2100 Temperature ° C. | H2200 Temperature ° C. | OSC (Sec) | Speed (rpm) | Flow Direction |
|---|---|---|---|---|---|---|---|---|---|---|---|
| 0 | Pre-Compression | 5 | Constant Mode 0 | | Gradient Mode 0 to 0.35 | Constant Mode 52 | Constant Mode 55 | 0 | 0 | Up |
| 1 | Compression | 55 | Constant Mode 40 h | | Gradient Mode 0.35 to 2 | Constant Mode 52 | Constant Mode 55 | 30 | 20 | Up |
| 2 | Compression | 25 | Gradient Mode 40 to 20 | | Gradient Mode 2 to 3 | Constant Mode 52 | Constant Mode 55 | 30 | 20 | Down |
| 3 | Main Extraction | 90 | Constant Mode 20 | | Constant Mode 3 | Constant Mode 52 | Constant Mode 55 | 30 | 20 | Down |

De-binding processing parameters using supercritical solvent extraction

TABLE 1-continued

De-binding processing parameters using supercritical solvent extraction

| Process Step | Duration (min) | P200 $CO_2$ (Kg/h) | A22 Pressure (MPa) | H2100 Temperature ° C. | H2200 Temperature ° C. | M220 OSC (Sec) | M220 Speed (rpm) | Flow Direction |
|---|---|---|---|---|---|---|---|---|
| 4 Main Extraction | 90 | Constant Mode 20 | Constant Mode 3 | Constant Mode 58 | Constant Mode 61 | 30 | 20 | Down |
| 5 Main Extraction | 90 | Constant Mode 20 | Constant Mode 3 | Constant Mode 62 | Constant Mode 65 | 30 | 20 | Down |
| 6 Depressurize | 40 | Constant Mode 0 | Gradient Mode 3 to 1 | Constant Mode 62 | Constant Mode 65 | 30 | 20 | Down |
| 7 Depressurize | 100 | Constant Mode 0 | Gradient Mode 1 to 0 | Constant Mode 62 | Constant Mode 65 | 0 | 0 | Down |
| 8 Depressurize | 10 | Constant Mode 0 | Constant Mode 0 | Constant Mode 52 | Constant Mode 55 | 0 | 0 | Up |
| 9 End | 0 | Constant Mode 0 | Constant Mode 0 | Constant Mode 50 | Constant Mode 54 | 0 | 0 | Up |
| 10 End | 0 | Constant Mode 0 | Constant Mode 0 | Constant Mode 50 | Constant Mode 54 | 0 | 0 | Up |

Sintering, Si-Infiltration and Densification

A second de-binding step was applied under flowing hydrogen up to 500° C. with a temperature ramping of about 1° C./min. The Si-infiltration was performed under vacuum using a fast ramping temperature (about 50° C./minute) to a temperature of 1650° C. (1700° C.). After 10 min an Ar-pressure of 9.5 MPa (95 bar) was applied when the body was fully infiltrated which helped in the densification i.e. increased the final density and reduced porosity. The diamond brown bodies were placed in hBN-coated graphite crucibles with silicon lumps in large excess (200% in weight, placed in the bottom of the crucible). The silicon used was Silicon 99 Refined —Si 30 015 from Elkem with a silicon content of 99.4 wt % and oxygen content of 0.004% analyzed by LECO and a with a particle size of 10-100 mm. After an additional 10 min at 1650° C. 9.5 MPa (95 bar) under argon, the samples were allowed to cool down freely.

Sintering and HIP-Infiltration Using a Zr-Capsule

Si-infiltration may optionally be achieved by hot isostatic gas pressure (HIP) processing and/or high pressure high temperature (HPHT) processing to apply high pressure and temperature to the diamond powders to provide melting and Si-infiltration The brown bodies may then be placed in a Zr-capsule with a sealed bottom and with a dense-packed silicon powder blend completely surrounding the brown bodies. The Zirconium capsule may be manufactured from a tube with a commercial grade Zr, a purity of ≥92.2 wt % and with Hf-content of ≤4.5 wt %. The Si-powder blend may be a mixture of 86 wt % Silgrain® coarse from Elkem with a purity of 99.5 wt % and with an oxygen content of 0.119 wt % analyzed by LECO and grain size of 0.2-0.8 mm and Silgrain HQ from Elkem with a purity of 98% and with an oxygen content of 0.059 wt % analyzed by LECO and a grain size between 20-300 microns. The tap density of the Si-blend may be about 1.36 g/cm$^3$, measured by filling a calibrated volume (Ford cup) with the Si-powder blend during subsequent manual tapping of the cup in the same way as performed during the filling of the capsules and then measuring the weight, which corresponds to about 58% of the theoretical sintered density of silicon. After filling the capsule, it may be sealed by welding. The sealed capsules may then be arranged in a HIP furnace and the temperature increased to 400° C. under vacuum. After a 30 min hold time at 400° C., the argon gas pressure may be rapidly raised to 4.0 MPa (40 bar) and then the temperature may be increased with 16°/min to 1300° C. At 1300° C. the pressure may be increased to 100 MPa (1000 bar) during roughly 55 minutes at constant temperature followed by a concurrent temperature and pressure increment until the maximum sintering temperature 1570° C. and the maximum pressure of 11.25 MPa (1125 bar) is reached after 20 min. The capsules may then be allowed to cool down freely during pressure release.

Blasting and Etching

Green bodies obtained following the Si-infiltration were then be processed to remove excess silicon from the surface and internally. Internal excess Si removal was achieved by introducing the green bodies to a bath containing 2% HF and 20% $HNO_3$ in an aqueous solution for about 24 hours to remove Si-residuals surrounding the inserts. External excess Si removal was achieved using a grit blaster with SiC grit. The SiC grit removed Si from the sintered body but did not abrade the body itself, indicating that the body was well sintered and had a very high hardness and abrasion resistance.

Quality Control

Density, CT and ocular control was used for all samples and the target density was ≥3.23 g/cm$^3$, 32 wt % diamond, 64 wt % SiC & 6 wt % Si corresponding to about 30 vol % diamond, 62 vol % SiC & 8 vol % Si, which is regarded as the minimum desired diamond content and maximum allowed residual Si content. It will be appreciated that Si has the lowest density and a decrease of free Si will have a preferred effect to increase the density. During the HIP-process a certain volume shrinkage occurs i.e., linear shrinkage of a few percent. The sintered bodies will also contain zirconium which will increase the sintered density significant compared to the purely Si-infiltrated parts. The density of the bodies were typically about 3.5 g/cm$^3$.

The sintered bodies were CT-scanned for defect detection. The CT-system used was a v|tome|x s240 from GE Sensing and Inspection Technologies, with the following settings: Magnification 9.1; Voxelsize (Resolution) 22 μm; X-ray voltage 80 kV; X-ray current 270 ρA; X-ray filter (Cu) 0.1 mm; Detector timing 200 ms; Detector averaging 3; Detector skip 1; Detector sensitivity 4; Number of projections 1200.

Sintered Diamond Composites

Example 1 (LCM-Built Cube)

A three dimensional cube green body was built from a slurry containing the PSD1 diamond feed according to the lithographic process described with reference to FIG. 1 and in accordance with the procedures under Slurry Preparation and Green Building. A layer building thickness of 50 μm was employed. The diamond density in the resulting green body was approximately 54% and was calculated as the mass of diamonds in the green body (polymerisable binders and other additions excluded) divided by the volume of the green body obtained divide by the X-ray density of diamonds (3.52 g/cm$^3$) multiplied by 100. The resulting green bodies were carefully de-bound in air using slow ramping temperature of 0.3° C./minute up to maximum de-binding temperature of 220° C. The de-binding process was purposefully not completed as it was desired to retain residual carbon in the brown body for strength (of the de-bound green). When infiltrating with a carbide forming infiltrant (silicon) the residual carbon will react and form carbides to reduce the amount of diamond consumed. The de-binding process was optimized according to the processing parameters as excessive residual carbon in the brown will impede infiltration resulting in macroporosity/graphitization particularly at the inner region of the brown body.

The brown body was then placed in the graphite cubicle and the sintering/Si-infiltration performed as detailed above, using 99.4% pure Silicon 99 Refined —Si 30 015 from Elkem with a particle size of 10-100 mm. After sintering the cube was treated by SiC grit blasting to remove residual Si on the surface, as detailed above. The cube was weighed and the density was determined using Archimedes' method with the result shown in table 2.

TABLE 2

Physical characteristics of LCM-built diamond composite cube (Example 1)

| mass green body (g) | mass brown body (g) | mass sintered body (%) | volume sintered body (cm$^3$) | sintered density Archimedes (g/cm$^3$) |
|---|---|---|---|---|
| 1.592 | 1.417 | 2.105 | 0.637 | 3.307 |

Figure 2:
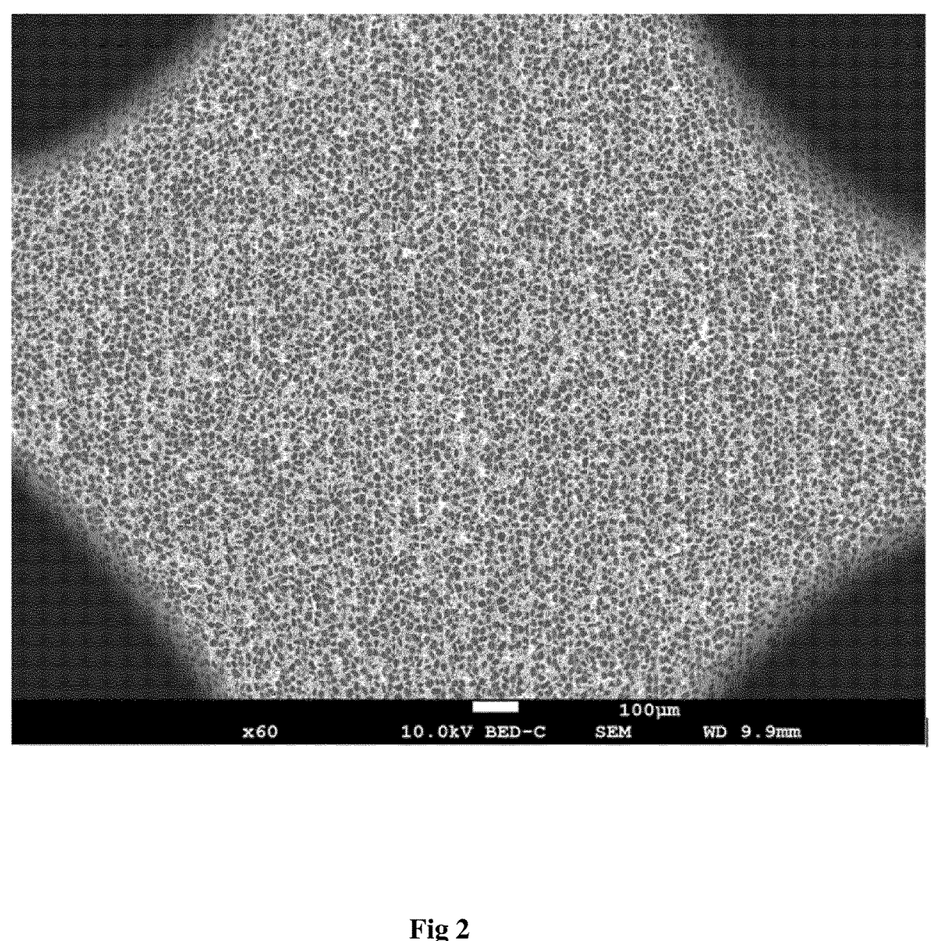
FIG. 2 is an SEM image at 60× magnification of a cubic diamond/silicon carbide composite according to one aspect of the present disclosure.
Figure 3:
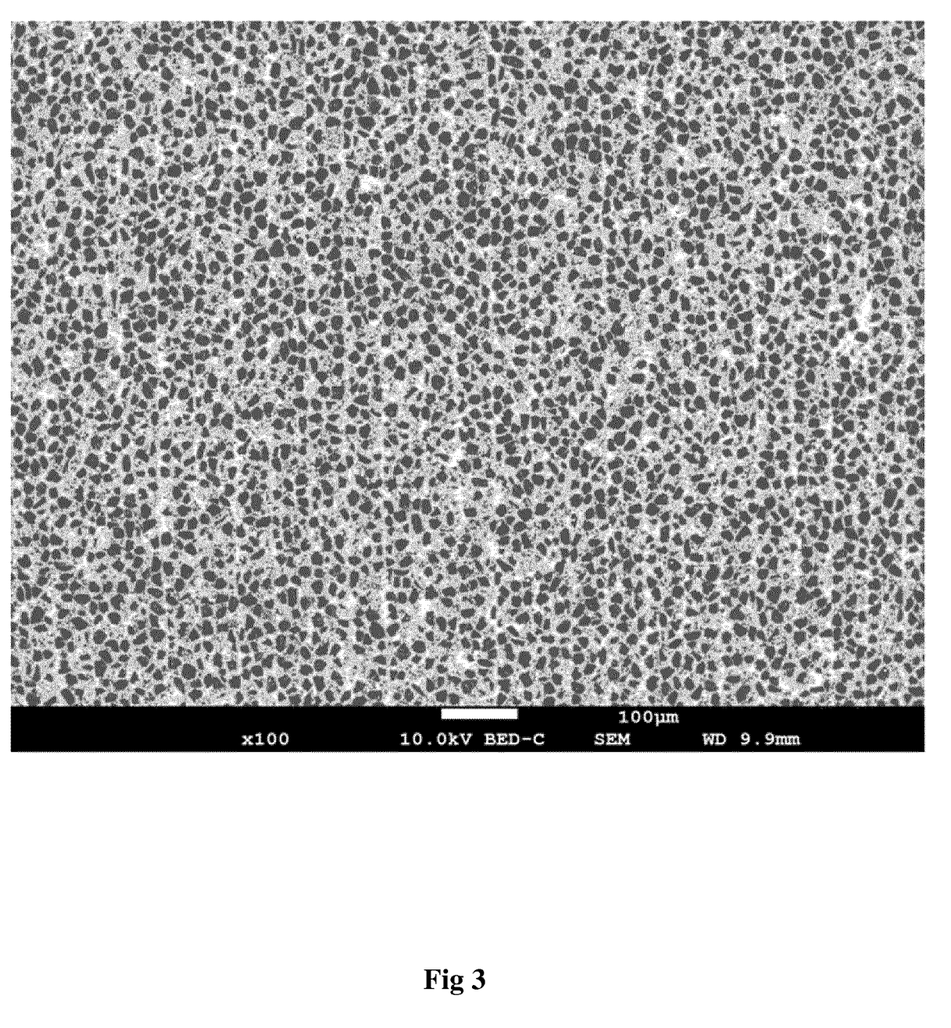
FIG. 3 is an SEM image at 100× magnification of a cubic diamond/silicon carbide composite according to one aspect of the present disclosure.

Sintered inserts were prepared by careful mechanical polishing of the insert tip to a depth of ~2 mm below the top, and a final polishing step was performed with 1 μm diamond paste. FIG. 2 and FIG. 3 are SEM images (of different magnification) of the cubic diamond-silicon carbide composites. It will be noted that the diamond grains are black and the silicon carbide phase is light grey, with residual silicon showing as white regions. It can be seen that the diamond distribution is uniform with no 'large' areas of residual silicon present. The images also clearly illustrate the printing layers within the resulting sintered composite body with each layer separated by narrow light lines/bands corresponding to the 50 μm layer thickness.

Example 2 LCM-Built Nozzle

A three-dimensional nozzle green body was constructed from a slurry containing the PSD1 diamond feed at 80 wt % with 20 wt % organic additives as detailed in example 1. A green body nozzle was constructed layerwise to comprise a total height of 12 mm with two negative parts of diameter 9.85 mm separated by an annular groove having a diameter 7.75 mm and a height 2.1 mm. The nozzle comprised an internal bore having a hole size diameter of 1.3 mm to 3 mm. The resulting green was carefully de-bound in air using a slow ramping temperature of 0.5° C./minute with 60 minute holding times at 150° C. and 190° C. before continuing to heat up to a maximum de-binding temperature of 240° C. via a temperature ramping of 0.3° C./minute. The brown body was then placed in the graphite cubicle and the sintering/Si infiltration performed as described above under 'Sintering— Si infiltration and densification' using 99.4% pure Silicon 99 Refined —Si 30 015 from Elkem with a particle size of 10-100 mm. After sintering, the nozzle was acid treated followed by SiC grit blasting to remove residual Si internally and on the surface, as detailed above. The nozzle was weighed and the density determined using Archimedes' method with results shown in table 3.

TABLE 3

Physical characteristics of LCM-built diamond composite nozzle (Example 2)

| mass green body (g) | mass brown body (g) | mass sintered body (%) | volume sintered body (cm$^3$) | sintered density Archimedes (g/cm$^3$) |
|---|---|---|---|---|
| 1.785 | 1.582 | 2.335 | 0.709 | 3.295 |

Surface roughness analysis was performed using a Wyko NT9100 on a 470.3×627.1 μm$^2$ surface. The magnification was 10.1 and the field of view 1.0 times. The results are shown in table 4

TABLE 4

Surface roughness of diamond composite nozzle (Example 2)

| Place of measurement | Sa (μm) | Sz (μm) | Stylus X Ra (μm) |
|---|---|---|---|
| OD (9.88 mm) | 2.15 | 20.62 | 1.05 |
| OD (7.75 mm) | 1.99 | 16.26 | 0.76 |

The outer dimensions of the sintered body in relation to the CAD-drawing were measured on different parts of the nozzle and was performed by scanning the outer surface of the whole body using a Mitutoyo CMM (Cordenat Measuring Machine) equipped with a Nikon laser head and employing Fokus software. The deviation from the CAD-model on the sintered part for the negative part with OD 9.88 mm was −0.076 mm to −0.040 mm and the deviation from the CAD-model for the green part with OD 7.75 mm was −0.031 to −0.016 mm. During the present infiltration and sintering process the size and shape of the de-bound green body is maintained and the dimensions of the sintered bodies are within at least 1.5% when compared to the built greens.

Example 3 LCM-Built Profiled Body

A three-dimensional profile body having a generally curved outer surface was built from slurry containing the PSD1 diamond feed at 80 wt % with 20 wt % organic additives as detailed in example 1. The resulting green were carefully de-bound in air using a slow ramping temperature of 0.5° C./minute with holding times at pre-determined temperatures to avoid cracks. No cracks were found in the brown when examined by LOM and X-ray CT. The brown body was then placed in the graphite cubicle and the sintering/Si infiltration performed as described above using 99.4% pure Silicon 99 Refined —Si 30 015 from Elkem with a particle size of 10-100 mm. After sintering, the profiled body was treated by SiC grit blasting to remove residual Si on the surface, as detailed above. The body was weighed and the density determined using Archimedes' method with results shown in table 5.

TABLE 5

Physical characteristics of LCM-built diamond profiled body (Example 3)

| mass green body (g) | mass brown body (g) | mass sintered body (%) | volume sintered body (cm³) | sintered density Archimedes (g/cm³) |
|---|---|---|---|---|
| 2.344 | 2.109 | 3.109 | 0.941 | 3.304 |

Surface roughness analysis was performed using a Wyko NT9100 on a 470.3×627.1 µm2 surface. The magnification was 10.1 and the field of view 1.0 times.

TABLE 6

Surface roughness of diamond composite profiled body (Example 3)

| Place of measurement | Sa (µm) | Sz (µm) | Stylus X Ra (µm) |
|---|---|---|---|
| Cutting edge | 1.76 | 14.72 | 1.01 |
| Plane surface 1 | 1.84 | 15.93 | 0.92 |
| Plane surface 2 | 1.86 | 19.73 | 0.87 |

The outer dimensions of the sintered body in relation to the CAD-drawing were measured on different parts of the profiled body and were performed by scanning the outer surface of the whole body using a Mitutoyo CMM (Cordenat Measuring Machine) equipped with a Nikon laser head and employing Fokus software. When comparing the dimension of the built greens with the dimensions of the sintered bodies the deviation from the CAD-model for the green body compared with the final obtained body when viewing the the outer dimensions of the radial part was −0.023 mm to −0.014 mm.

Figure 4:
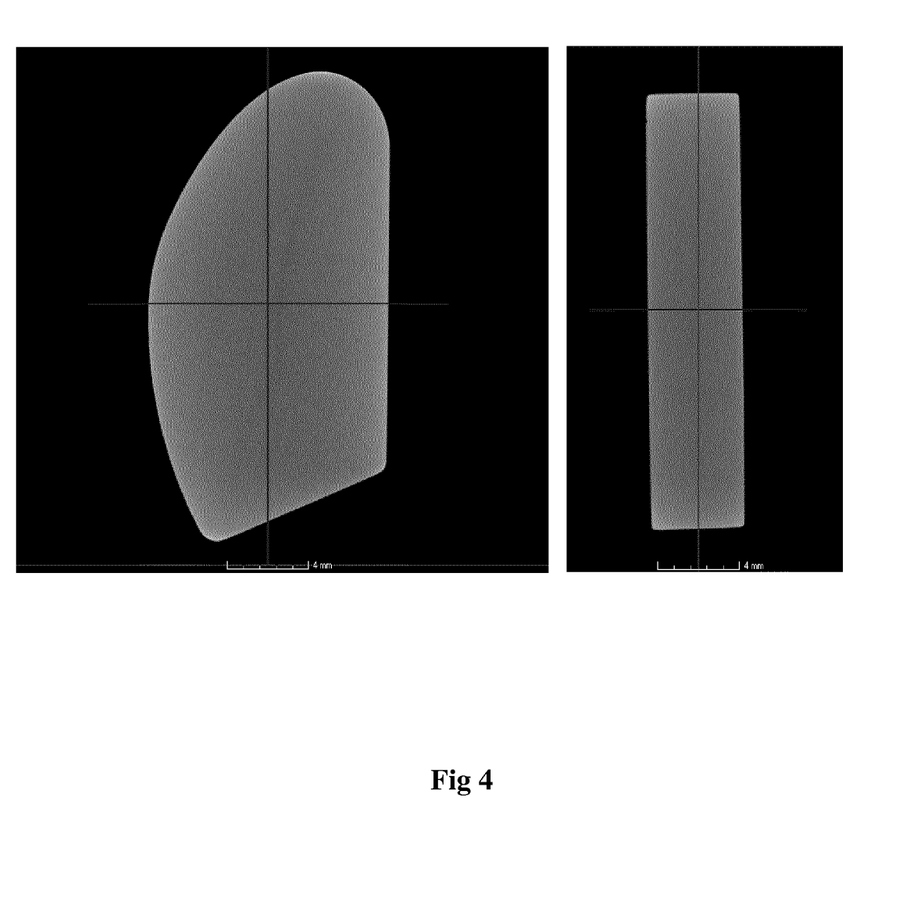
FIG. 4 is a CT-image of a lithographic built profiled body according to one aspect of the present disclosure.

FIG. 4 is a CT-image of the LCM built profiled body according to example 3 which shows that the sintered body is free from internal defects as cracks and macroporosity.

Example 4 LCM-Built Cube De-Bound in Supercritical Solvent

A three dimensional cube green body was built from a slurry containing the PSD1 diamond feed according to Example 1. As a departure from Example 1, de-binding was performed by extracting the LCM-binders using supercritical $CO_2$ for 24 hours at a temperature of 60° C. and a pressure of 30 MPa (300 bar) according to table 1 and the de-binding process under De-binding (supercritical solvent). No cracks or internal defects were found in the brown or in the sintered part when examined by LOM and X-ray CT. The body was weighed and the density determined using Archimedes' method with results shown in table 7.

TABLE 7

Physical characteristics of LCM-built diamond composite (Example 4)

| mass green body (g) | mass brown body (g) | mass sintered body (%) | volume sintered body (cm³) | sintered density Archimedes (g/cm³) |
|---|---|---|---|---|
| 1.113 | 1.029 | 1.459 | 0.443 | 3.291 |

Figure 5:
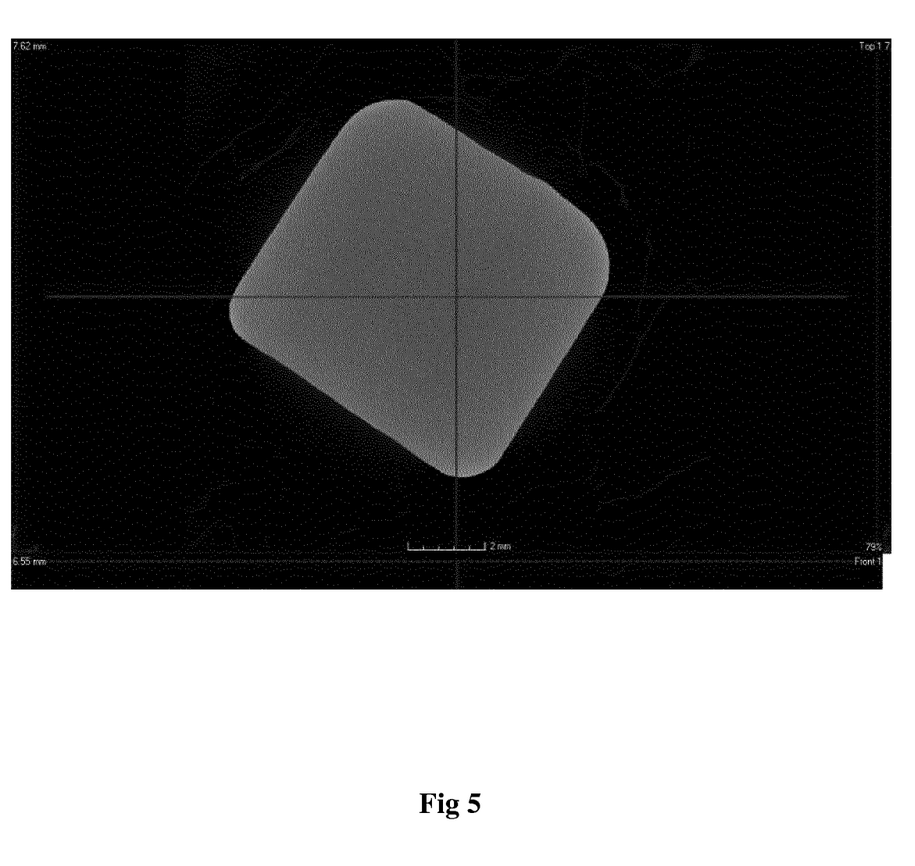
FIG. 5 is a CT-image of a lithographic built, supercritical de-bound and sintered cube according to one aspect of the present disclosure.

FIG. 5 is a CT-image of the LCM-built supercritical de-bound and sintered cube according to example 4.

Example 5 LCM-Built Profiled Body

A three-dimensional profile body having a generally curved outer surface was built from slurry containing the PSD2 diamond feed at 80 wt % with 20 wt % organic additives as detailed in example 1. As a departure from Example 1, de-binding was performed by extracting the LCM-binders using supercritical $CO_2$ for 24 hours at a temperature of 60° C. and a pressure of 30 MPa (300 bar) according to table 1 and the de-binding process under De-binding (supercritical solvent). No cracks or internal defects were found in the brown body when examined by LOM and X-ray CT. The brown body was then placed in the graphite cubicle and the sintering/Si infiltration performed as described above using >99% pure CZ-Silicon wafers from Okmetic. After sintering, the profiled body was treated by SiC grit blasting to remove residual Si on the surface, as detailed above. The body was weighed and the density determined using Archimedes' method with results shown in table 8.

TABLE 8

Physical characteristics of LCM-built diamond profiled body (Example 5)

| mass green body (g) | mass brown body (g) | mass sintered body (%) | volume sintered body (cm³) | sintered density Archimedes (g/cm³) |
|---|---|---|---|---|
| 2.439 | 2.241 | 3.073 | 2.126 | 3.236 |

Figure 6:
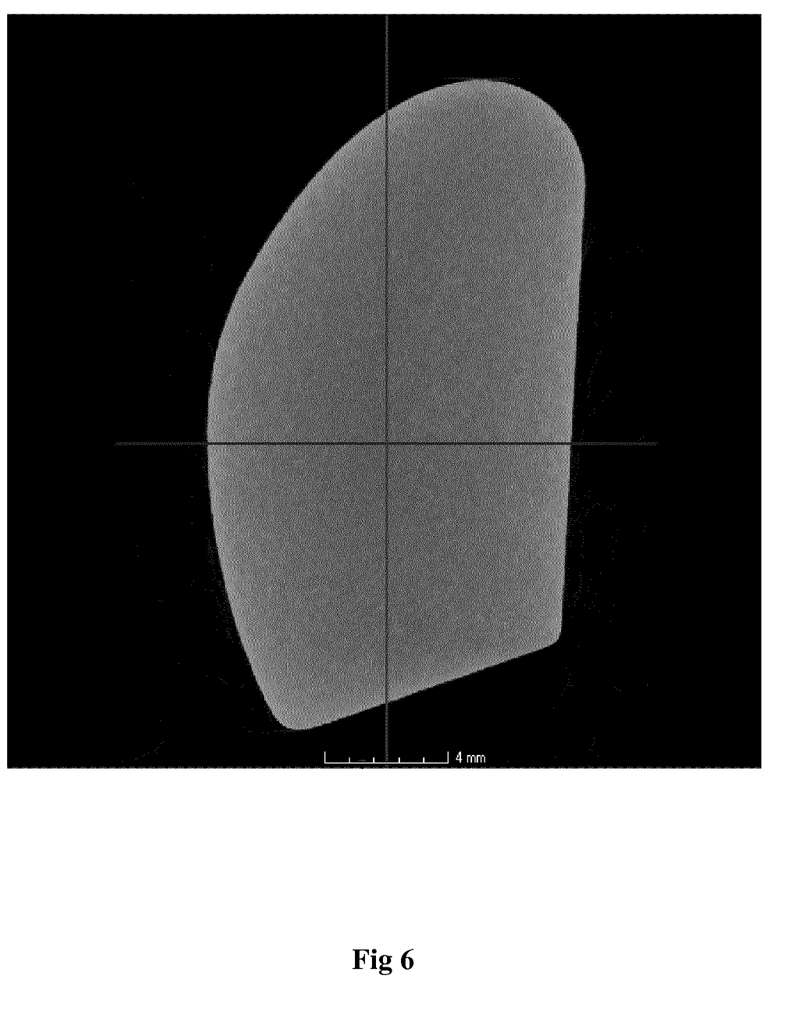
FIG. 6 is a CT-image of a lithographic built profiled body according to one aspect of the present disclosure.

FIG. 6 is a CT-image of the LCM-built supercritical de-bound and sintered profiled body according to example 5 which shows that the sintered body is free from internal defects such as cracks and macro porosity.

Low Pressure Sintering—Infiltration in Vacuum at 1650° C. (Comparative Study)

Example 6 Surface Roughness of Prior Art Manufactured Parts

A Homogenous slurry was prepared using the PSD1 diamond mixture described Diamond Powder Preparation and then adding PEG1500 and PEG4000 as temporary organic binders, with de-ionized water as the fluid. The slurry was spray granulated to produce granules for pressing and the amount of organic binders in the powder was 9.26 wt % which corresponds to 23 vol %. Granules were used in uni-axial pressing of green bodies in the shape of tool tips (buttons) typically used in mining operations (rock drilling) to a green density as high as possible with the used compaction technique. The force applied for the compaction of the green bodies was typically 30-50 kN and the press tool was made from a high wear resistance cemented carbide grade. The relative diamond density in the green bodies was around 60%. The relative diamond density in percentage was calculated as the mass of diamonds in the green body (temporary organic binders and other additions excluded) divided by the volume of the green body obtained from the press tool drawing divided by the X-ray density of diamonds (3.52 g/cm³), multiplied by 100. Depending on the compaction technique and the shape of the body the density can vary slightly between different parts of the green body. The green bodies were de-bound as described in De-binding (heat treatment) to create a brown body (white body) of enough strength for further handling.

The diamond brown bodies were placed in hBN-coated graphite crucibles with silicon lumps in large excess (200% in weight, placed in the bottom of the crucible). The silicon used was Silicon 99 Refined —Si 30 015 from Elkem with a silicon content of 99.4 wt % and oxygen content of 0.004% analyzed by LECO and a with a particle size of 10-100 mm. The brown body was then placed in the graphite cubicle and the sintering/Si-infiltration performed as detailed above, using 99.4% pure Silicon 99 Refined —Si 30 015 from Elkem with a particle size of 10-100 mm. After sintering the cube was treated by SiC grit blasting to remove residual Si on the surface, as detailed above. The bodies was weighed and the density was determined using Archimedes' method with the result shown in table 9.

Surface roughness analysis were carried and found in table 10. The top of the dome of the insert was than polished by diamond grits and the microstructure was investigated using SEM.

TABLE 9

Physical characteristics of uni-axial pressed diamond profiled body (Example 6)

| mass green body (g) | mass brown body (g) | mass sintered body (%) | volume sintered body (cm$^3$) | sintered density Archimedes (g/cm$^3$) |
|---|---|---|---|---|
| 7.707 | 7.016 | 11.126 | 3.365 | 3.303 |

TABLE 10

Surface roughness of diamond composite mining insert (Example 6)

| Place of measurement | Sa (μm) | Sz (μm) | Stylus X Ra (μm) |
|---|---|---|---|
| OD (16 mm) | 1.56 | 14.39 | 0.79 |
| Cutting edge, top of dome | 5.19 | 36.92 | 2.36 |

Figure 7:
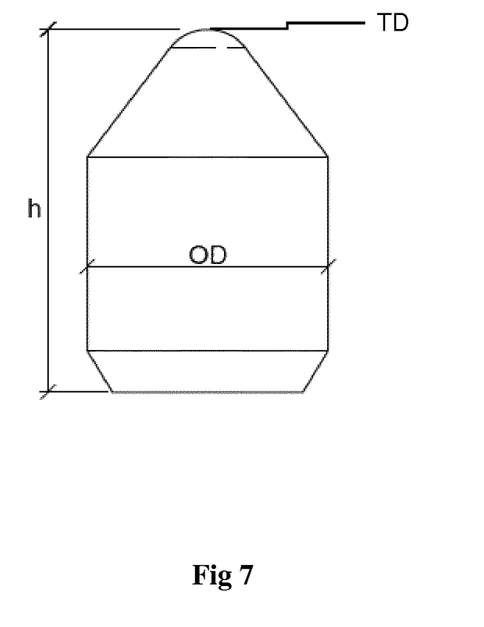
FIG. 7 is a schematic illustration of a mining insert.
Figure 8:
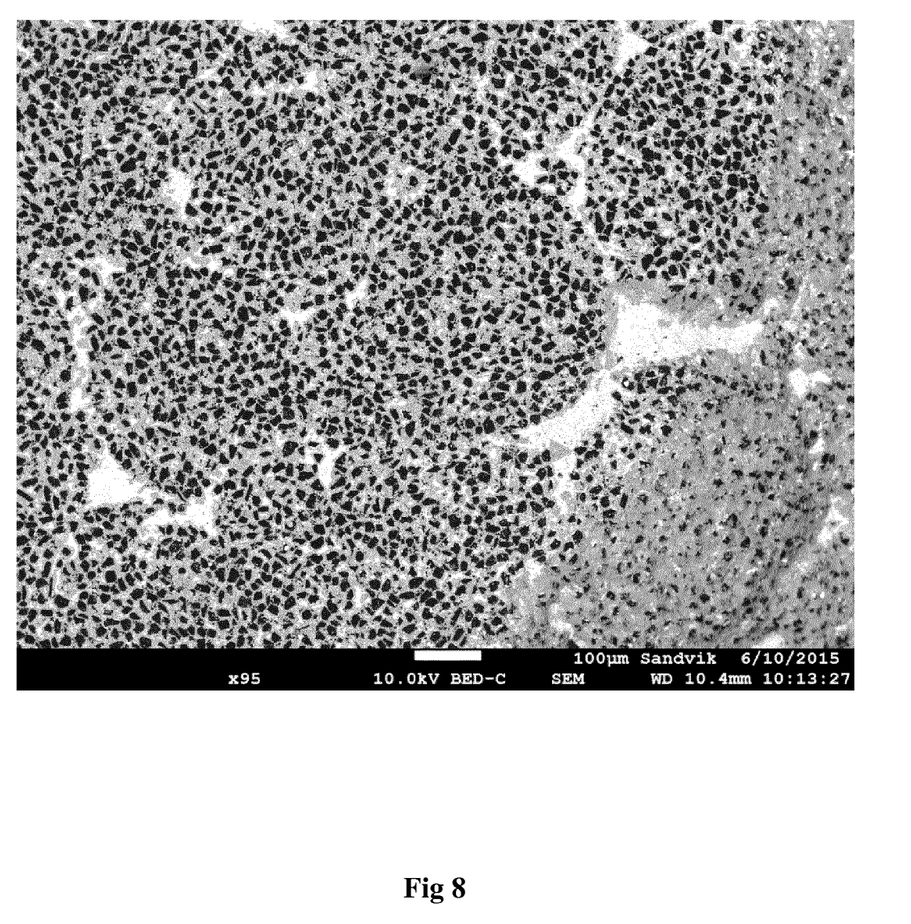
FIG. 8 is backscattered SEM-image at 95X of a sintered structure of a partly polished cutting edge of the mining insert of FIG. 7 according to a prior art preparation method.

FIG. 7 is a drawing of a mining insert as described in example 6 where the cutting edge (tope of dome) (TD, and the outer diameter (OD) and height (h) are indicated. FIG. 8 is a backscattered SEM-image 95 X of the sintered structure of the partly polished cutting edge (top of dome) of the mining insert in Example 6. In the image large white Si-lakes as well as un-crushed granules are clearly visible. (Diamond=black, SiC=light grey, residual Si=white).

The invention claimed is:

1. A method of preparing a diamond composite with a layered structure comprising:
    preparing a slurry containing a polymerisable binder, an initiator and diamond particles;
    forming a layered structure green body by stepwise irradiation curing of the slurry containing diamond particles, binder and initiator;
    forming a white body comprising at least 30 vol % diamond particles by de-binding the layered structure green body;
    introducing an infiltrant to the white body; and
    sintering the white body by heating the white body from an initial stage up to a maximum sintering temperature by incremental temperature increases at a rate of 10 to 60° C./min at a first pressure to form a layered microstructure having diamond rich layers with binder matrix rich layers in between, wherein the diamond rich layers are in the range of 25 to 200 microns and the binder matrix rich layers are in the range of 1 to 15 microns, and a content of the diamond particles in the diamond composite article being between 30 and 65 vol %, wherein the binder in the binder matrix rich layers is SiC.

2. The method as claimed in claim 1, wherein the diamond particles have a particle size of less than or equal to 200 μm.

3. The method as claimed in claim 1, wherein the diamond particles have a particle size of less than or equal to 100 μm.

4. The method as claimed in claim 1, wherein the diamond particles have a bi-modular or multi-modular particle size distribution and at least one fraction of diamond particles has a particle size of less than 30 μm and at least one fraction of diamond particles has a particle size of less than 100 μm.

5. The method as claimed in claim 1, wherein the step of de-binding includes heating the green body up to a first de-binding temperature via incremental temperature increases, wherein the de-binding temperature is in a range of from 200° C. to 600° C. and the incremental temperature increases are at increments of 0.1 to 2° C./min.

6. The method as claimed in claim 1, wherein the step of de-binding includes exposing the green body to a supercritical fluid.

7. The method as claimed in claim 1, further comprising continuing to heat the white body in a further stage at a second pressure greater than the first pressure.

8. The method as claimed in claim 7, wherein the maximum sintering temperature during the initial stage is in the range of from 850 to 1750° C.

9. The method as claimed in claim 7, wherein the second pressure at the further stage is at least 50% greater than the first pressure at the initial stage.

* * * * *